United States Patent
Fulkerson et al.

(10) Patent No.: US 11,253,379 B2
(45) Date of Patent: Feb. 22, 2022

(54) STENTS HAVING PROTRUDING DRUG-DELIVERY FEATURES AND ASSOCIATED SYSTEMS AND METHODS

(71) Applicant: ReFlow Medical, Inc., San Clemente, CA (US)

(72) Inventors: John Fulkerson, Rancho Santa Margarita, CA (US); Isa Rizk, San Clemente, CA (US); Jihad Ali Mustapha, Ada, MI (US); Teodoro S. Jimenez, Jr., Aliso Viejo, CA (US)

(73) Assignee: ReFlow Medical, Inc., San Clemente, CA (US)

( * ) Notice: Subject to any disclaimer, the term of this patent is extended or adjusted under 35 U.S.C. 154(b) by 11 days.

(21) Appl. No.: 16/294,806

(22) Filed: Mar. 6, 2019

(65) Prior Publication Data

US 2019/0201219 A1 Jul. 4, 2019

Related U.S. Application Data

(63) Continuation of application No. 15/470,688, filed on Mar. 27, 2017, now Pat. No. 10,258,487, which is a
(Continued)

(51) Int. Cl.
*A61F 2/90* (2013.01)
*A61F 2/848* (2013.01)
(Continued)

(52) U.S. Cl.
CPC ................ *A61F 2/90* (2013.01); *A61F 2/848* (2013.01); *A61L 31/16* (2013.01); *A61F 2/82* (2013.01);
(Continued)

(58) Field of Classification Search
CPC .... A61F 2/848; A61F 2002/8483; A61F 2/90; A61F 2/82; A61F 2/86; A61F 2/95;
(Continued)

(56) References Cited

U.S. PATENT DOCUMENTS

| | | |
|---|---|---|
| 6,126,685 A | 10/2000 | Lenker et al. |
| 6,197,013 B1 | 3/2001 | Reed |

(Continued)

FOREIGN PATENT DOCUMENTS

| | | |
|---|---|---|
| CN | 101247777 | 8/2008 |
| CN | 101420913 | 4/2009 |

(Continued)

OTHER PUBLICATIONS

International Search Report and Written Opinion for International Application No. PCT/US2016/056688 filed Oct. 12, 2016, Applicant: ReFlow Medical, Inc., dated Jan. 26, 2017, 15 pages.

(Continued)

*Primary Examiner* — Seema Mathew
(74) *Attorney, Agent, or Firm* — Morgan, Lewis & Bockius LLP

(57) ABSTRACT

Expandable elements having drug-delivery features and associated systems and methods are disclosed herein. In one embodiment, a drug-eluting stent includes a radially expandable cylindrical frame having a plurality of struts. The frame is transformable between a low-profile delivery state and an expanded deployed state. A plurality of drug-delivery features are carried by one of the struts and configured to deliver a drug to a treatment site within the patient or piercing through the tissue wall to break the constricting of the vessel wall inwardly. When the frame is in the expanded state within a body lumen of the patient, the drug-delivery features extend radially outwardly away from the strut and (Continued)

are configured to engage and, in some arrangements, pass through a wall of the body lumen.

20 Claims, 19 Drawing Sheets

Related U.S. Application Data continuation of application No. 15/292,072, filed on Oct. 12, 2016, now Pat. No. 10,172,729.

(60) Provisional application No. 62/240,320, filed on Oct. 12, 2015.

(51) Int. Cl.
*A61L 31/16* (2006.01)
*A61F 2/95* (2013.01)
*A61F 2/82* (2013.01)
*A61F 2/86* (2013.01)

(52) U.S. Cl.
CPC . *A61F 2/86* (2013.01); *A61F 2/95* (2013.01); *A61F 2002/8483* (2013.01); *A61F 2002/9528* (2013.01); *A61F 2220/0016* (2013.01); *A61F 2250/0023* (2013.01); *A61F 2250/0067* (2013.01); *A61F 2250/0068* (2013.01); *A61F 2250/0098* (2013.01); *A61L 2300/416* (2013.01); *A61L 2300/44* (2013.01)

(58) Field of Classification Search
CPC .............. A61F 2/013; A61F 2002/823; A61F 2250/0059; A61F 2250/0067; A61F 2250/0035

See application file for complete search history.

(56) References Cited

U.S. PATENT DOCUMENTS

| | | |
|---|---|---|
| 6,290,728 B1 | 9/2001 | Phelps et al. |
| 6,398,757 B1 | 6/2002 | Varenne |
| 6,425,915 B1 | 7/2002 | Khosravi et al. |
| 6,800,089 B1 | 10/2004 | Wang |
| 6,808,518 B2 | 10/2004 | Wellman |
| 6,949,080 B2 | 9/2005 | Wolf et al. |
| 6,991,617 B2 | 1/2006 | Hektner et al. |
| 6,991,643 B2 | 1/2006 | Saadat |
| 7,041,127 B2 | 5/2006 | Ledergerber |
| 7,122,043 B2 | 10/2006 | Greenhalgh et al. |
| 7,258,697 B1 | 8/2007 | Cox et al. |
| 7,273,493 B2 | 9/2007 | Ledergerber |
| 7,470,252 B2 | 12/2008 | Mickley |
| 7,500,986 B2 | 3/2009 | Lye et al. |
| 7,520,903 B2 | 4/2009 | Ferreyrol |
| 7,651,696 B2 | 1/2010 | Bates |
| 7,753,945 B2 | 7/2010 | Bruun et al. |
| 7,846,198 B2 | 12/2010 | Hogendijk |
| 7,963,935 B2 | 6/2011 | Cormier |
| 7,993,386 B2 | 8/2011 | Elliott |
| 8,007,470 B2 | 8/2011 | Shirley et al. |
| 8,024,851 B2 | 9/2011 | Barr et al. |
| 8,034,098 B1 | 10/2011 | Callas et al. |
| 8,109,904 B1 | 2/2012 | Papp |
| 8,187,316 B2 | 5/2012 | Kuppurathanam et al. |
| 8,202,311 B2 | 6/2012 | Demetriades |
| 8,221,482 B2 | 7/2012 | Cottone et al. |
| 8,337,542 B2 | 12/2012 | Jantzen et al. |
| 8,414,909 B2 | 4/2013 | Wang |
| 8,623,066 B2 | 1/2014 | Looi et al. |
| 8,690,822 B2 | 4/2014 | Papp |
| 8,764,712 B2 | 7/2014 | Melsheimer |
| 8,764,814 B2 | 7/2014 | Solem |
| 8,771,340 B2 | 7/2014 | Densford |
| 8,778,012 B2 | 7/2014 | Matheny |
| 8,881,365 B2 | 11/2014 | Kuppurathanam et al. |
| 8,956,398 B2 | 2/2015 | George et al. |
| 9,138,233 B2 | 9/2015 | Anderson |
| 9,149,496 B2 | 10/2015 | Matheny |
| 9,198,687 B2 | 12/2015 | Fulkerson |
| 9,198,784 B2 | 12/2015 | Andreas et al. |
| 9,220,618 B2 | 12/2015 | Igaki et al. |
| 9,283,078 B2 | 3/2016 | Roels et al. |
| 9,445,929 B2 | 9/2016 | Longo et al. |
| 9,480,826 B2* | 11/2016 | Schneider ......... A61M 25/1027 |
| 9,566,367 B2 | 2/2017 | Stekker et al. |
| 9,597,206 B2 | 3/2017 | Seddon et al. |
| 9,675,473 B2 | 6/2017 | Clerc et al. |
| 9,724,220 B2 | 8/2017 | Rasmussen |
| 9,770,575 B2 | 9/2017 | Wesselmann et al. |
| 9,814,608 B2 | 11/2017 | Clerc et al. |
| 9,855,160 B2 | 1/2018 | Armstrong et al. |
| 10,004,615 B2 | 6/2018 | Sherry |
| 10,039,659 B2 | 8/2018 | Bialas et al. |
| 10,076,399 B2* | 9/2018 | Davidson ............. A61B 17/221 |
| 10,307,273 B2 | 6/2019 | Rubesch et al. |
| 10,342,684 B2 | 7/2019 | Firstenberg et al. |
| 10,441,404 B2* | 10/2019 | Leon-Yip ............. A61B 17/221 |
| 10,575,972 B2* | 3/2020 | Kim ........................ A61F 2/848 |
| 10,617,435 B2* | 4/2020 | Vale ......................... A61F 2/013 |
| 10,668,188 B2 | 6/2020 | Wang |
| 10,842,498 B2* | 11/2020 | Vale .................... A61B 17/1214 |
| 10,893,869 B2* | 1/2021 | Choubey .......... A61B 17/12036 |
| 11,123,089 B2* | 9/2021 | Ma ....................... A61B 17/221 |
| 2001/0020151 A1 | 9/2001 | Reed et al. |
| 2002/0090388 A1 | 7/2002 | Humes et al. |
| 2002/0193864 A1 | 12/2002 | Khosravi et al. |
| 2003/0055491 A1 | 3/2003 | Schwartz et al. |
| 2003/0105514 A1 | 6/2003 | Phelps et al. |
| 2003/0195458 A1 | 10/2003 | Phelps et al. |
| 2003/0216803 A1 | 11/2003 | Ledergerber |
| 2004/0064093 A1 | 2/2004 | Hektner et al. |
| 2004/0098116 A1 | 5/2004 | Callas et al. |
| 2004/0161446 A1 | 8/2004 | Bhat |
| 2005/0010275 A1 | 1/2005 | Sahatjian et al. |
| 2005/0033411 A1 | 2/2005 | Wu et al. |
| 2005/0043783 A1 | 2/2005 | Amis et al. |
| 2005/0049692 A1 | 3/2005 | Numamoto et al. |
| 2005/0096731 A1 | 5/2005 | Looi |
| 2005/0171599 A1 | 8/2005 | White |
| 2006/0089703 A1 | 4/2006 | Escamilla et al. |
| 2006/0129229 A1 | 6/2006 | Fukaya et al. |
| 2006/0136049 A1 | 6/2006 | Rojo |
| 2006/0287709 A1 | 12/2006 | Rao |
| 2007/0038288 A1 | 2/2007 | Lye |
| 2007/0191811 A1 | 8/2007 | Berglund |
| 2007/0213761 A1 | 9/2007 | Murphy |
| 2008/0071178 A1 | 3/2008 | Greenland |
| 2009/0062839 A1 | 3/2009 | Kurrus |
| 2010/0042206 A1 | 2/2010 | Yadav |
| 2011/0002953 A1 | 1/2011 | Harris et al. |
| 2011/0004237 A1 | 1/2011 | Schneider et al. |
| 2011/0257723 A1 | 10/2011 | McNamara |
| 2012/0041412 A1 | 2/2012 | Roth |
| 2012/0083872 A1 | 4/2012 | Schneider et al. |
| 2012/0095542 A1 | 4/2012 | Tekulve |
| 2012/0310327 A1 | 12/2012 | Mchugo |
| 2013/0253573 A1 | 9/2013 | Agnew |
| 2014/0058420 A1* | 2/2014 | Hannes ............ A61B 17/12113 606/158 |
| 2015/0051708 A1* | 2/2015 | Anderson .............. A61B 17/08 623/23.7 |
| 2015/0148731 A1 | 5/2015 | McNamara |
| 2015/0148889 A1 | 5/2015 | Angel et al. |
| 2015/0359622 A1 | 12/2015 | Matheny |
| 2015/0359932 A1 | 12/2015 | Matheny |
| 2015/0359933 A1 | 12/2015 | Matheny |
| 2015/0374481 A1* | 12/2015 | Johnsen .................... A61F 2/01 606/200 |
| 2016/0095599 A1 | 4/2016 | Jose et al. |
| 2016/0296321 A1 | 10/2016 | Roels et al. |
| 2017/0086992 A1* | 3/2017 | Ferrera ................. A61M 25/09 |
| 2018/0303594 A1 | 10/2018 | Eller et al. |
| 2018/0360589 A1 | 12/2018 | Nolan et al. |

(56) References Cited

U.S. PATENT DOCUMENTS

| | | | |
|---|---|---|---|
| 2019/0167456 A1 | 6/2019 | Collins et al. | |
| 2019/0365549 A1* | 12/2019 | Folan | A61F 2/95 |
| 2020/0139017 A1 | 5/2020 | Meyer-Kobbe et al. | |
| 2020/0171214 A1 | 6/2020 | Dietz | |
| 2020/0214825 A1* | 7/2020 | Gassier | A61F 2/07 |
| 2020/0345523 A1* | 11/2020 | Michalak | A61F 2/848 |
| 2021/0145617 A1* | 5/2021 | Doi | A61F 2/90 |

FOREIGN PATENT DOCUMENTS

| | | |
|---|---|---|
| EP | 1506747 | 2/2005 |
| EP | 2414021 | 2/2012 |
| EP | 2531229 | 12/2012 |
| EP | 2545887 | 1/2013 |
| EP | 2550030 | 1/2013 |
| JP | 2004-523275 | 8/2004 |
| JP | 2006-505364 | 2/2006 |
| JP | 2010-520785 | 6/2010 |
| JP | 2014-012223 | 1/2014 |
| WO | WO 03/003948 | 1/2003 |
| WO | WO 2004/032800 | 4/2004 |
| WO | WO 2004/043509 | 5/2004 |
| WO | WO 2004/058100 | 7/2004 |
| WO | WO 2008/112458 | 9/2008 |
| WO | WO 2008/125145 | 10/2008 |
| WO | WO 2018/213352 | 11/2018 |
| WO | WO 2020/101675 | 5/2020 |
| WO | WO 2020/172560 | 8/2020 |

OTHER PUBLICATIONS

Extended European Search Report from European Patent Application No. 16856132.2, dated Apr. 16, 2019, 7 pages.
Chinese Office Action from Chinese Patent Application No. 201680072455.1, dated Jul. 18, 2019, 13 pages including English language translation.
Chinese Office Action from Chinese Patent Application No. 201680072455.1, dated Apr. 10, 2020, 11 pages including English language translation.
European Office Action from European Patent Application No. 16856132.2, dated Mar. 27, 2020, 5 pages.
Australian Examination Report Australian Patent Application No. 2016339033, dated Jun. 12, 2020, 4 pages.
Japanese Office Action from Japanese Patent Application No. 2018-538539 dated Aug. 4, 2020, 18 pages including English language translation.
Chinese Office Action from Chinese Application No. 201680072455.1, dated Oct. 26, 2020, 12 pages including English language translation.
Australian Notice of Acceptance from Australian Patent Application No. 2016339033, dated Mar. 26, 2021, 3 pages.
Japanese Office Action from Japanese Patent Application No. 2018-538539 dated Mar. 17, 2021, 9 pages including English language translation.

* cited by examiner

STENTS HAVING PROTRUDING DRUG-DELIVERY FEATURES AND ASSOCIATED SYSTEMS AND METHODS

CROSS-REFERENCE TO RELATED APPLICATION

This application is a continuation of U.S. patent application Ser. No. 15/470,688, filed on Mar. 27, 2017, which is a continuation of U.S. patent application Ser. No. 15/292,072, filed on Oct. 12, 2016, now issued as U.S. Pat. No. 10,172,729, which claims the benefit of U.S. Provisional Application No. 62/240,320, filed on Oct. 12, 2015, entitled DRUG-ELUTING STENTS HAVING PROTRUDING DRUG-DELIVERY FEATURES AND ASSOCIATED SYSTEMS AND METHODS, the contents of each of which are herein incorporated by reference in their entireties.

TECHNICAL FIELD

The present technology relates generally to expandable elements, such as stents or scaffolds having spikes, flails, or other protruding features for delivering drugs and/or penetrating target tissue within a human patient.

BACKGROUND

A variety of devices can be used to deliver drugs at desired treatment locations within a patient. For example, a drug-eluting stent (DES) can be positioned at the location of a stenosis (arterial narrowing) caused by arteriosclerosis. DESs generally include a drug containing polymer coated over a metal stent or scaffold, or a bioresorbable stent or scaffold composed of a drug-containing polymer. After a DES is delivered to a treatment location within a body lumen, it is expanded against a vessel wall and the drug is released via direct contact with the wall. Direct delivery of the drug to the vessel wall enables significantly lower doses than those required via other delivery means (e.g., pills or injections). However, depending on the design of the underlying stent or scaffold, 85% or more of the stented vessel wall area may not be in contact with the stent struts. Accordingly, significant diseased portions of the vessel wall may not receive a desired dose or delivery of the drug will not be uniform throughout the treatment site. Additionally, portions of the DES may be in contact with blood, arterial plaque and/or with other fluid or materials within the vessel lumen that are not intended delivery sites for the drug. These issues can result in drug tissue concentrations that are lower than desired or less uniform than desired.

Drug-eluting balloons (DEBs), and non drug-eluting balloons, provide an alternative to DESs, and can address some of the limitations discussed above. For example, DEBs can also be delivered to a desired treatment location and expanded against a vessel wall to release a drug. DEBs, however, can include a coating of the drug over an entire surface area of the balloon that expands to be in uniform contact with the vessel wall. Accordingly, DEBs can provide a more uniform dose to the adjacent vessel tissue. Additionally, when used in conjunction with angioplasty, the drug can be delivered at the location and time of any vessel damage that occurs during the procedure. Even so, DEBs also have several limitations. For example, during the delivery of the drug (i.e., when the balloon is inflated), blood flow in the associated vessel is stopped or severely obstructed, and no other treatment devices can be passed through the vessel. Additionally, both DEBs and existing DESs fail to provide drug-delivery at all locations along an adjacent vessel wall. Specifically, uneven vessel walls, obstructions, contours, or other features can prevent the balloon surface or stent struts from reaching portions of the vessel wall. Moreover, existing DESs and DEBs do not provide for drug-delivery into the vessel wall (i.e., penetration of the vessel wall for drug-delivery within the tissue itself).

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

The following disclosure describes various embodiments of expandable structures, such as stents or scaffolds, having spikes, flails, or other protruding features for delivering drugs and/or penetrating target tissue within a human patient, and associated systems and methods. The drug-delivery features can be integrally formed with expandable element, or may include separate features protruding from a strut or other member of the expandable element positioned to engage and/or penetrate a vessel wall. For example, several embodiments configured in accordance with the present technology include expandable structure with drug-delivery features for delivering drugs to deep intimal layers and/or medial layers of vessels. In some embodiments, the drug-delivery features can include spikes protruding from one or more struts or portions of the expandable structure. The spikes can be configured to penetrate the vessel wall. In additional embodiments, the drug-delivery features can include angular protrusion(s) extending from one or more struts. Such angular protrusions are expected to provide better contact with the vessel wall, moving past obstructions or other interfering material to more effectively deliver drugs to target tissue. Additionally, the angular protrusions can increase the surface area of the drug-delivery features in contact with the vessel wall, thereby providing for a more uniform delivery of the drug. Still other embodiments may eliminate particular components and/or procedures.

Certain details are set forth in the following description and FIGS. 1-9K to provide a thorough understanding of various embodiments of the disclosure. To avoid unnecessarily obscuring the description of the various embodiments of the disclosure, other details describing well-known structures and systems often associated with expandable structures, drug-delivery features, and the components or devices associated with the manufacture of such structures are not set forth below. Moreover, many of the details and features shown in the Figures are merely illustrative of particular embodiments of the disclosure. Accordingly, other embodiments can have other details and features without departing from the spirit and scope of the present disclosure. A person of ordinary skill in the relevant art will therefore understand that the present technology, which includes associated devices, systems, and procedures, may include other embodiments with additional elements or steps, and/or may include other embodiments without several of the features or steps shown and described below with reference to FIGS. 1-9K. Furthermore, various embodiments of the disclosure can include structures other than those illustrated in the Figures and are expressly not limited to the structures shown in the Figures.

I. DRUG-ELUTING STENTS AND OTHER STRUCTURES AND ASSOCIATED SYSTEMS AND METHODS

Figure 1:
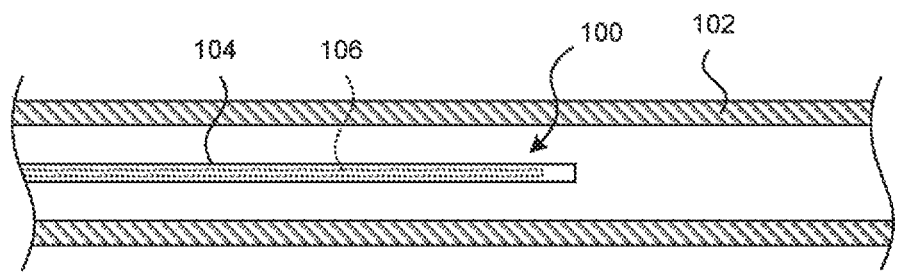
FIG. 1 is a partially schematic side view of a portion of a drug delivery system in a delivery state (e.g., low-profile or collapsed configuration) within a body lumen and configured in accordance with an embodiment of the present technology.

FIG. 1 is a partially schematic side view of a portion of a drug delivery system 100 ("the system 100") configured in accordance with an embodiment of the present technology. In the arrangement shown in FIG. 1, the system 100 is in a delivery state (e.g., low-profile or collapsed configuration) within a body lumen 102 (e.g., blood vessel) of a human patient. The system 100 includes, for example, a catheter 104 and a drug-eluting stent 106 carried in a delivery/collapsed state within a distal portion of the catheter 104. Although a stent is illustrated, it will be appreciated that embodiments of the present technology can also include cages, meshes, balloons, membranes, tubular structures, circumferential bodies, expandable elements, expandable membranes, expandable structures, expandable tubular structures, and circumferentially expandable catheter tips with and without guidewire lumens.

The catheter 104 is configured for intravascular delivery through the body lumen 102 to position the drug-eluting stent 106 at a desired treatment location. Additionally, several embodiments can provide for detachment of a stent or other structure including the drug-delivery features. For example, in several embodiments, a wire or attachment member 108 (shown in FIG. 2A) can release the stent 106 via mechanical, thermal, electrical or other means. In some embodiments, the drug-eluting stent 106 can be operatively coupled to a circular or non-circular longitudinal member configured to release and/or recapture the drug-eluting stent 106 in the system 100. The member can be coupled, either directly or indirectly, to a frame (111 of FIG. 2A) of the drug-eluting stent. In some of these embodiments, the stent 106 or other structure can be designed for permanent placement within a patient.

Figures 2A, 2B:
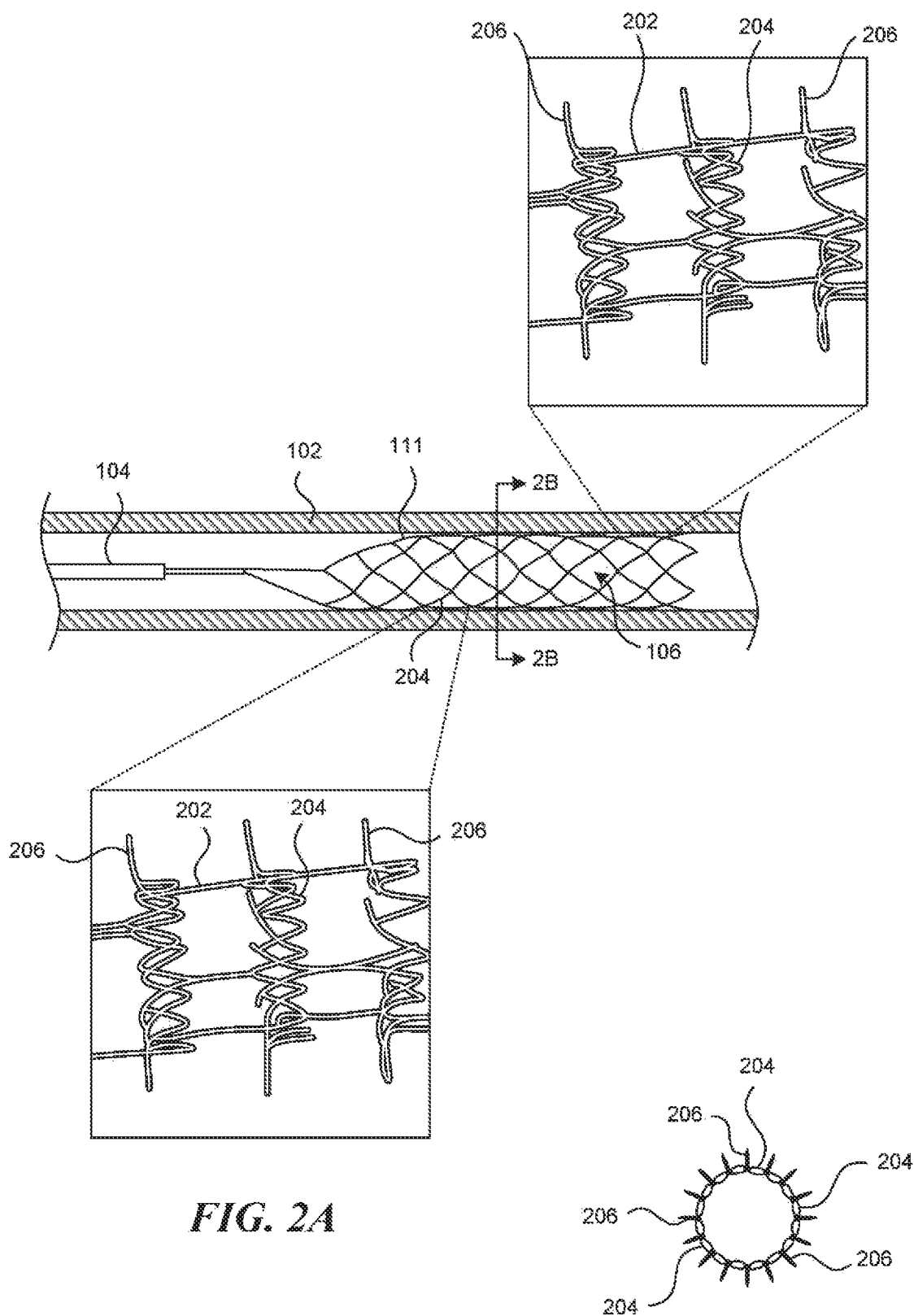
FIG. 2A is a side view of the portion of the drug delivery system of FIG. 1 in a partially deployed state (e.g., expanded configuration) within the body lumen and configured in accordance with an embodiment of the present technology.
FIG. 2B is a cross-sectional view of a portion of the drug delivery system of FIG. 2A taken along line 2B-2B.

FIG. 2A is a partially schematic side view of the system 100 of FIG. 1 in a partially deployed state (e.g., expanded configuration) within the body lumen 102. In the illustrated embodiment of FIG. 2A, the drug-eluting stent 106 has been advanced from a distal end of the catheter 104 and positioned adjacent a desired treatment site. The stent 106 includes a plurality of struts 204 forming a radially expandable cylindrical frame 111 and members engaging with and extending between two or more rows of struts. As illustrated, the struts 204 of the expanded drug-eluting stent 106 are in apposition with the walls of the body lumen 102. Referring to the blown-up portions of FIG. 2A, the drug-eluting stent 106 further includes a plurality of drug-delivery features 206 carried by the struts 2204. Several embodiments can be designed for application of a drug onto the stent or the drug-delivery features that are configured to receive a drug and release the drug once the stent is expanded at the desired treatment site. FIG. 2B is a cross-sectional view of a portion of the drug delivery system of FIG. 2A taken along line 2B-2B. As illustrated in FIG. 2B, the drug-eluting stent 106 includes a plurality of struts 204 having plurality of drug-delivery features 206 carried by the struts 204. The drug-delivery features 206 are integrally formed portions of the struts 204, disposed across at least a portion of an outer dimension of the stent 106, and extending radially outward away from the stent 106 toward the target portion of the body lumen.

The drug-eluting stent 106 can be a self-expanding structure. In other embodiments, the drug-eluting stent 106 can be coupled to a balloon or other suitable techniques and/or structures known to those of skill in the art may be used to transform the drug-eluting stent 106 from the low-profile delivery state to the deployed/expanded state shown in FIG. 2A. In addition, the drug-eluting stent 106 can be operatively coupled to an actuation mechanism, such as a mechanical actuation mechanism, configured to position, expand, retract, re-position, and/or remove the drug-eluting stent 106.

The frame 111, struts 204, and/or drug-delivery features 112 can be composed of or formed from a variety materials including, e.g., nitinol, cobalt chromium, stainless steel, any of a variety of other metals or metal alloys, or a combination thereof. The frame 111, struts 204, and/or drug-delivery features 112 may also be composed of or formed from bioresorbable biodegradable, nanoporous or non-bioresorbable, non-biodegradable, non-nanopourous materials including, e.g., one or more polymers, plastic materials, etc., or a combination thereof. In some embodiments, the frame 111 and the struts 204 can be formed from a bioresorbable material and the drug-delivery features 112 can be formed from a non-bioresorbable material, such as nitinol. In these embodiments, the drug-delivery features 112 can remain engaged with or penetrating a portion of the body lumen after the expanded frame 111 and struts 204 bio-resorb. After the expanded frame 111 and struts 204 bio-resorb, the body lumen where the drug-eluting stent 106 had been expanded is no longer partially occluded by the frame 111 and the struts 204 allowing for larger volumes of fluids, such as aqueous pharmaceutical compositions, to pass through the body lumen and contact the luminal wall. The drug-delivery features 112 may also be formed of a bio-resorbable material and, once the drug-eluting stent 106 has bio-resorbed, the spaces in the body lumen wall vacated by the drug-delivery features 112 can be contacted by the fluids passing through the lumen. In this way, the drug-eluting stent 106 can increase a surface area of the lumen wall contacted by the fluid.

The material(s) for forming the frame 111, struts 204, and/or drug-delivery features 112 can be selected based on mechanical and/or thermal properties, such as strength, ductility, hardness, elasticity, flexibility, flexural modulus, flexural strength, plasticity, stiffness, emissivity, thermal conductivity, specific heat, thermal diffusivity, thermal expansion, any of a variety of other properties, or a combination thereof. If formed from a material having thermal properties, the material can be activated to deliver thermal treatment to the desired treatment site.

Regardless of the material, the frame 111, struts 204, and/or drug-delivery features 112 can be formed from a tube or a wire, such as a solid wire, by laser cutting or other suitable techniques. When formed from the wire, a portion of the wire can be removed by chemical etching or another suitable method to create an inner dimension of the drug-eluting stent 106.

In accordance with the present technology, drug-eluting stents 106 (e.g., the frame 111 and the struts 204) can be sized and shaped for placement within various body lumens, including blood vessels, while not rupturing the vessel. For example, several stents and other structures configured in accordance with the present technology can have radial strength that allows for features of the body lumen (e.g., vessel wall) to receive drugs without dissection or damage thereto. Vessels in which the drug-eluting stents 106 may be sized and shaped for placement include arteries, such as coronary arteries, peripheral arteries, carotid arteries, circle of willis, anterior cerebral artery, middle cerebral artery, posterior cerebral artery, any of the lenticulostriate arteries, renal arteries, femoral arteries, veins, such as cerebral veins, saphenous veins, arteriovenous fistulas, or any other vessel that may contain a treatment site. Drug-eluting stents 106 can have a variety of shapes, including a cube, a rectangular prism, a cylinder, a cone, a pyramid, or variations thereof.

The stent 106 and other structures having drug-delivery features configured in accordance with the present technology can include a variety of dimensions (in both the low-profile delivery state and expanded deployed state). These embodiments can provide for expansion that enables usage in a variety of situations covering a wide range of dimensions. Regardless of the shape, drug-eluting stents 106 can have a length of about 0.25 mm, about 0.5 mm, about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 30 mm, about 40 mm, about 50 mm, about 60 mm, about 70 mm, about 80 mm, about 90 mm, or about 100 mm. In addition, a drug-eluting stent 106 shaped into a cube, a rectangular prism, or a pyramid can have a width of about 0.25 mm, about 0.5 mm, about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, or about 30 mm. Moreover, a drug-eluting stent 106 shaped into a cylinder or a cone can have a diameter of about 0.25 mm, about 0.5 mm, about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, about 30 mm, about 35 mm, about 40 mm, or about 50 mm. The width or the diameter of the drug-eluting stent 106 can decrementally decrease along a length of the stent. In addition, the drug-eluting stent 106 can be sized and shaped to prepare the body lumen for certain procedures, such as a drug-eluting stent placement procedure.

Profiles of the drug-eluting stents or other structures can be sized such that the drug-eluting stents or other structures are compatible with a wide range of catheter sizes. Embodiments in accordance with the present technology can include drug-eluting stents or other structures designed to receive a guidewire, such as guidewires having a diameter of 0.010, 0.014, 0.018, 0.035, or 0.038 inch. In several embodiments, the stent or scaffold structure can be sized and designed for delivery via a micro-catheter that it is pushed through. In some embodiments, stents or structures configured in accordance with the present technology can be incorporated into a delivery system, including modular or single unit delivery systems.

The drug-eluting stent 106 can include a marking for visualization of the stent 106 within the body lumen, such as one or more radiopaque markers. The radiopaque markers can be formed from Clearfil Photo Core PLT®, tantalum, titanium, tungsten, barium sulfate, and zirconium oxide, or another suitable radiopaque marking. The markings can be formed on a proximal portion of the drug-eluting stent 106, a distal portion, an intermediate portion, or a combination thereof. The markings can be a band, a coil, a clip, filled into one or more portions of a tube in the stent, plated onto one or more portions of the stent, or a combination thereof. Regardless of the type of marking, the marking can be coined, swaged, wrapped, or encased along, or onto any portion of the stent.

Stents and other structures configured in accordance with the present technology can be flexible enough to track through various anatomical features, including those having a curvature. The flexible properties of the stent and other structures can be provided by the material from they are formed. In addition, flexible properties can also be provided by fracturing one or more of the members engaging with and extending between two or more rows of struts. Additionally, the drug-eluting stent or other structure can be readily deployed and expanded, and retracted and contracted. The drug-eluting stent or other structure can also be readily repositioned within a vessel or other lumen.

II. DRUG-DELIVERY FEATURES OF DRUG-ELUTING STENTS AND OTHER STRUCTURES AND ASSOCIATED SYSTEMS AND METHODS

In the embodiment shown in FIGS. 2A and 2B, the drug-eluting stent 106 includes drug-delivery features 206 carried by the strut 204. The drug-delivery features 206 may also be carried by more than one strut 204, the frame 111, or a combination thereof. The drug-delivery features 206 may be integrally formed with the struts 204, for example by bending or twisting a portion of one or more struts and/or the frame 111 away from a longitudinal axis of the stent 106 or, alternatively, the drug-delivery features 206 may be separate, discrete components that are attached to desired locations along the struts 204 and/or the frame 111. As illustrated, the drug-delivery features 206 are integrally formed with the struts 204. However, as described below with reference to FIGS. 3A-3D, the drug-delivery features 206 may have a variety of different shapes, sizes, and configurations. The drug-delivery features disclosed herein enhances engagement with and/or penetration of the lumen wall, provides enhanced drug-delivery, and allows for better treatment at the desired location. In other embodiments, such as non drug-delivery stents, the drug-delivery features 206 can be protruding members.

In several embodiments, a drug-eluting compound is coated onto at least a portion of the drug-delivery features. The drug-eluting compound can be a synthetic or biological polymer coated into a variety of different patterns and thicknesses suitable for delivering the drug contained therein. In other embodiments, the drug-delivery features themselves may be composed of drug-eluting materials. The drug carried by the drug-eluting compound and/or the drug-delivery features in accordance with the present technology can be any drug suitable for treating the treatment site in which the drug-eluting stent will be placed and may or may not include an excipient. For example, the drug can be an anti-proliferative, an anti-neoplastic, a migration inhibitor, an enhanced healing factor, an immunosuppressive, an anti-thrombotic, a blood thinner, or a radioactive compound. Examples of anti-neoplastics include, but are not limited to, siroliums, tacrolimus, everolimus, leflunomide, M-predniso-lone, dexamethasone, cyclosporine, mycophenolic acid, mizoribine, interferon, and tranilast. Examples of anti-proliferatives include, but are not limited to, taxol/paclitaxel, actinomycin, methotrexate, angiopeptin, vincristine, mitmy-cine, statins, c-myc antisense, Abbot ABT-578, RestinASE, 2-chloro-deoxyadenosine, and PCNA ribozyme. Examples of migration inhibitors, but are not limited to, include batimistat, prolyl hydroxylase, halofunginone, c-preteinase inhibitors, and probucol. Examples of enhanced healing factors include, but are not limited to, BCP 671, VEGF, estradiols, NO donor comounds, and EPC antibodies. Examples, of radioactive compounds include, but are not limited to, strontium-89 chloride (Metastron®), samarium-153 (Quadramet®), radium-223 dichloride (Xofigo®), yttrium-90, and iodine-131. In some embodiments, the drug-eluting compound and/or the drug-delivery features can carry more than one drug.

Figure 3A:
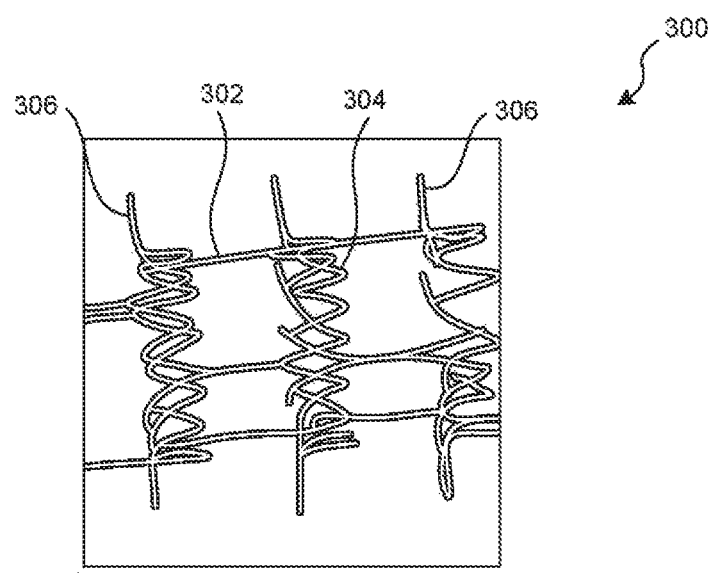
FIGS. 3A-3D are isometric views of portions of drug-eluting expandable structures having drug-delivery features configured in accordance with embodiments of the present technology.
Figure 3B:
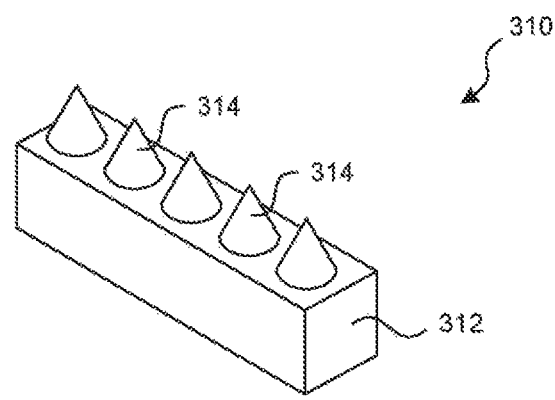
Figure 3C:
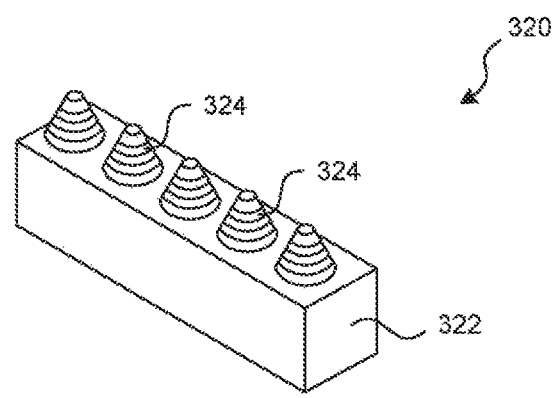
Figure 3D:
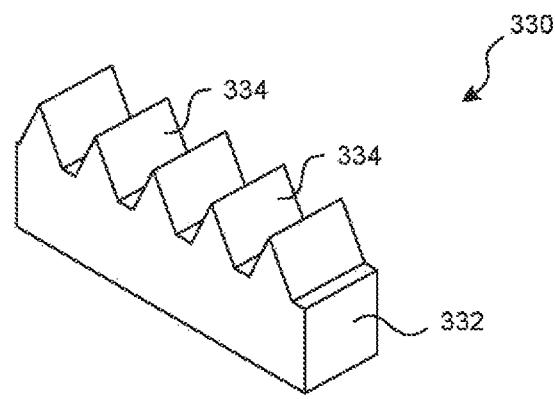

FIGS. 3A-3D are isometric views of portions of protruding members, such as drug-delivery features, carried by drug-eluting stents configured in accordance with additional embodiments of the present technology. These protruding members may be used with the drug-eluting stent 106 described above with reference to FIGS. 1 and 2, or other suitable drug-eluting and non drug-eluting stents configured in accordance with the present technology. FIG. 3A, for example, illustrates a portion of a stent 300 including a frame 302 and a plurality of struts 304 having protruding members 306 (e.g., spikes, sharpened/tapered members, barbs, needles) configured to engage with and/or penetrate a portion of the body lumen, such as a vessel (not shown). The protruding members 306 are integrally formed portions of the struts 304 and extend radially outward away from the stent 300 toward the target portion of the body lumen. In the embodiment illustrated in FIG. 3B, for example, a drug-eluting stent 310 includes a strut 312 having drug-delivery features 314 carried thereon. In this embodiment, the drug-delivery features 314 are pointed conical protrusions. In some embodiments, the pointed conical protrusions can provide for penetration through a body lumen wall (e.g., a vessel wall) to deliver drugs directly into target tissue beyond the vessel wall. Vessels and target tissues are described above with reference to FIGS. 2A and 2B. FIG. 3C illustrates a portion of a drug-eluting stent 320 with a strut 322 carrying drug-delivery features 324. In this embodiment, the drug-delivery features 324 are pointed conical protrusions having ribbed surfaces and flattened tops. In some embodiments, the textured (e.g., ribbed) surfaces of the protruding and conical drug-delivery features 324 are expected to provide greater surface area for drug-delivery. While only illustrated on conical drug-delivery features 324, any drug-delivery features can include a textured surface such as a ribbed surface (vertical, horizontal, radial, or circular relative to a longitudinal plane of the drug-delivery feature), a cross-hatched surface, an isotropic surface, or other surface types suitable for providing greater surface area for drug-delivery. FIG. 3D illustrates a portion of a drug-eluting stent 330 including a strut 332 carrying drug-delivery features 334. In the illustrated embodiment, drug-delivery features 334 are wedge shaped protrusions configured to engage/penetrate through a vessel wall for drug-delivery.

Although the illustrated embodiments of FIGS. 2 and 3A-3D include protruding members, such as, drug-delivery features having a variety of shapes, it is to be understood that other embodiments can include drug-delivery features having alternative shapes to those shown in these Figures. For example, the drug-delivery features can be sized and shaped for placement within various body lumens, including vessels as described herein. The sizes and shapes can be selected to achieve a desired engagement with or penetration of certain features (e.g., target tissues) of the body lumen in which the drug-eluting stent 106 will be placed. The drug-delivery features can have a number of shapes, including but not limited to, a cube, a square, a rectangular prism, a cylinder, a circle, a cone, a pyramid, curved-spikes, or other pointed shape. Any of these shapes can have flat, dull, pointed, and/or sharp distal portions.

The drug-delivery features can be sized and shaped to engage with and/or penetrate an occlusion, a neointima, an intima, an internal elastic lamina (IEL) a media, an external elastic lamina (EEL), an adventitia, or a combination thereof. The drug-delivery features can also be sized and shaped to engage with and/or penetrate a tissue and/or structure adjacent to the body lumen in which the drug-eluting stent 106 is to be placed while not rupturing the body lumen. For example, the drug-eluting stent 106 can include square drug-delivery features sized and configured to penetrate into the intima and/or the media of a body lumen, pointed drug-delivery features sized and configured to penetrate and extend into the media, and/or the IEL. In addition, drug-delivery features can be configured to bend in one or more directions relative to a longitudinal axis of the drug-eluting stent to engage with and/or penetrate a portion of the body lumen described herein. In several embodiments, the drug-delivery features can penetrate deeper into the wall of a diseased body lumen, such as a vessel, compared to a stent lacking drug-delivery features. In addition, the drug-eluting stent can allow for blood to flow even while in the expanded position and with drug-eluting on-going.

Various drug-delivery features described herein can deliver drugs deeper into a vessel wall than possible via angioplasty balloons or other existing devices. In addition to carrying one or more drugs for treatment of the site, the drug-delivery features can also carry a molecule suitable for degrading a portion of the occlusion, neointima, and/or intima to allow the drug-delivery features to penetrate deeper in to the vessel wall than without the molecule. For example, the molecule suitable for degradation can be an enzyme, such as elastase, collagenase, or a proteinase, such as, metalloproteinases, serine proteinases, cysteine proteinases, extracellular sulfatases, hyaluronidases, lysyl oxidases, lysyl hydroxylases, or a combination thereof.

Further, it will also be appreciated that drug-eluting stents configured in accordance with the present technology can carry one or more drug-delivery features on one or more portions of the stent. For example, the drug-eluting stents can carry about 5 drug-delivery features, about 10 drug-delivery features, about 15 drug-delivery features, about 20 drug-delivery features, about 30 drug-delivery features, about 40 drug-delivery features, about 50 drug-delivery features, about 60 drug-delivery features, about 70 drug-delivery features, about 80 drug-delivery features, about 90 drug-delivery features, or about 100 drug-delivery features. The drug-delivery features can be carried by the frame 111, the struts 204, or a combination thereof. The number of drug-delivery features can vary depending upon, for example, the target treatment site, the type of drug being delivered, and size of the stent, etc. In addition, the drug-delivery features carried by the stent can be different types of the drug-delivery features disclosed herein.

Figure 4A:
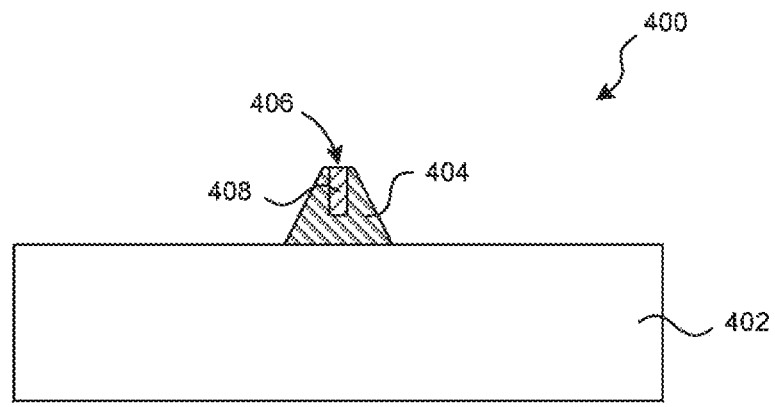
FIG. 4A is a cross-sectional view of a portion of a drug-eluting stent illustrating a drug-delivery feature configured in accordance with yet another embodiment of the present technology.

FIG. 4A is a cross-sectional view of a portion of a drug-eluting stent 400 including a strut 402 carrying drug-delivery feature 404 configured in accordance with yet another embodiment of the present technology. In the illustrated embodiment, the drug-delivery feature 404 includes a reservoir 406, and a drug 408 carried by the reservoir 406. The reservoir 406 can at least partially contain the drug 408 and protect it from being prematurely released (e.g., via scraping during delivery of the associated stent through a catheter). Once positioned against a body lumen wall (e.g., a vessel wall), tissue and/or fluid can interact with the drug-delivery feature 404 to dissolve the drug 408 and selectively release it from the reservoir 406. In other embodiments, the drug-delivery feature can be configured to deliver the drug via a variety of means once the drug-eluting stent is expanded. Drug-delivery feature 404 is accordingly expected to provide an effective means for selectively delivering a drug to a desired location, while reducing inadvertent loss or release of drugs. In other embodiments, the drug-eluting stent can include more than one drug-delivery feature, or a drug-delivery feature having more than one reservoir. In several embodiments, the stent including drug-delivery features configured in accordance with the present technology can have the drug-delivery feature, such as the coating or the reservoir, concealed (e.g., recessed) until the stent is positioned at the treatment site. Once positioned at the target site, the drug-delivery feature can be revealed (e.g., expanded/projected, etc.) during and/or after expansion of the stent. This is expected to reduce any loss of the drug carried by the drug-delivery feature during delivery to the treatment site.

Figure 4B:
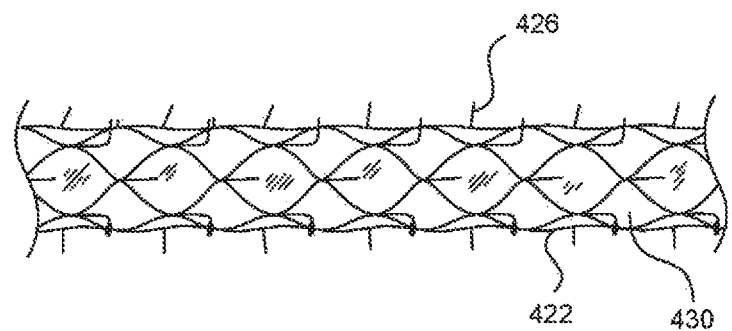
FIG. 4B is a side view of a portion of a drug-eluting stent configured in accordance with yet another embodiment of the present technology.

Referring next to FIG. 4B, in some embodiments, the drug-eluting stents can further include a material 430 (e.g., PTFE, Dacron, polyamides, such as nylon and/or polyurethane based materials, silicone, etc.) positioned over a stent, scaffold or other structure 422 having drug-delivery features 426 covering at least a portion of the outer surface area. In some embodiments, the material 430 covers the entire outer surface area. The material 430 can be a mesh or a braid. In some embodiments, the material 430 can be configured to increase a surface area of the stent useful for providing additional surface area of the stent for coating with a drug. In other embodiments, the material 430 can further be configured to allow blood flow through the inner diameter of the stent and/or limit blood flow to an outer dimension of the stent. In additional embodiments, the material 430 can create a barrier between fluid flow (e.g., blood flow) and the drug-delivery locations. In addition, the material 430 can be configured to prevent debris from the wall of the body lumen from entering the bloodstream. In such embodiments, the associated systems and devices can be used for temporary dissection tacking or coverage of a region that may have been perforated during a procedure.

III. ADDITIONAL EMBODIMENTS OF STENTS AND OTHER STRUCTURES AND ASSOCIATED SYSTEMS AND METHODS

The embodiments described herein provide a structure with a means for delivering drugs to a specific region within a body lumen, such as the vasculature, while still allowing fluid (e.g., blood) to flow through the treatment area where the structure has been placed and/or other devices or treatment means within the adjacent body lumen. In some embodiments, the drug-eluting stents are configured not to limit fluid flow (e.g., blood flow) through the body lumen (e.g., vessel). In addition, the stent can be configured to prepare the body lumen for treatment, by raking the stent, pulling the stent, turning the stent, or a combination thereof, proximal or distal to the treatment site. In other embodiments, the drug-eluting stent can be configured to rotate when mechanical force is applied.

The systems disclosed herein can provide for adjustment, recapture, and redeployment of the associated stents or other structures, allowing a practitioner to more effectively to treat a desired region more accurately and deliberately. In several embodiments, the stent or other delivery structure can be deployed for a temporary period (e.g., for less than 24 hours), and then retracted and removed. The drug-eluting stent can also be configured to post-dilate when removed from the body lumen. In other embodiments, the stent or other delivery structure can be deployed for a long-term temporary period (e.g., for less than 2 weeks, less than one month, less than 6 months, less than one year), and then retracted and removed. In some embodiments, a different stent or delivery structure can be deployed after a first stent or delivery structure has been retraced and removed. The duration of deployment and duration after removal before deployment of the different stent or delivery structure can vary from minutes, to hours, to days, to weeks, to months, or to years. In these embodiments, removal of the first stent or delivery structure and deployment of a different stent or delivery structure can occur once, twice, three times, four times, five times, six times, seven times, eight times, nine times, or ten times. Moreover, the embodiments described herein can allow for a lower profile system than currently available balloons.

While many embodiments of the stents and/or structures described herein include drug-eluting stents, additional embodiments of the expandable elements, such as stents and/or structures, can include non drug-eluting stents and/or non drug-eluting structures. In these embodiments, the non drug-eluting stents may include one or more protruding members, such as spikes. The spikes can be configured to engage with and/or penetrate a portion of the body lumen or vessel. For example, the spikes can penetrate the vessel wall, thereby reducing and/or eliminating an elasticity of the vessel wall. In these embodiments, the protruding members can be configured to prevent the vessel wall from progressing inward toward the lumen and restricting and/or constricting flow therein. The protruding members can be integrally formed with the struts, or disposed on the surface of the struts, extending radially outward from the struts toward the target tissue.

IV. ADDITIONAL EXAMPLES

The following examples are illustrative of several embodiments of the present technology. In these examples, a drug-eluting stent was placed within a vessel of a human patient post mortem. Three different types of stents were used: (a) a metal stent having square drug-delivery features, (b) a metal stent having round drug-delivery features, and (c) a metal stent having sharpened/tapered drug-delivery features. Stents having square or rectilinear drug-delivery features measured about 115 µm by 100 µm, stents having round or rounded drug-delivery features measured about 650 µm in diameter, and stents having sharpened/tapered drug-delivery features measured about 870 µm long and about 193 µm wide at the widest portion.

A. Example 1—Stents Having Sharpened/Tapered Drug-Delivery Features Engage with the External Elastic Lamina In this example, a stent having sharpened/tapered drug-delivery features was placed within a blood vessel of a human cadaver. Following placement of the sharpened/tapered drug-delivery feature stent, the vessel was removed from the cadaver, embedded in plastic, and sliced into cross-sections of a thickness suitable for histology. The cross-sections were stained using an Elastic Masson Trichrome stain, imaged, and evaluated for the positioning of the pointed drug-delivery feature stent in the vessel.

Figure 5A:
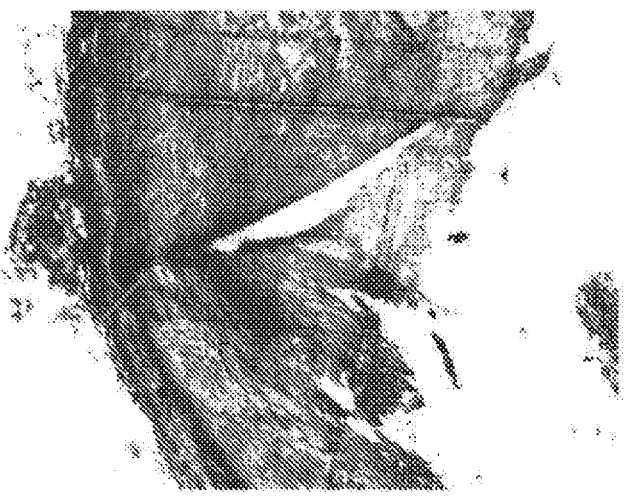
FIGS. 5A-5C are cross-sectional images of a portion of a blood vessel having a drug-eluting stent configured in accordance with an embodiment of the present technology expanded therein.
Figure 5B:
Figure 5C:

FIGS. 5A-5C include histology images taken after placement of the stent having the sharpened/tapered drug-delivery features within the vessel of the cadaver. FIG. 5A, for example, depicts a sharpened/tapered drug-delivery feature penetrated through the neointima, IEL, media, and engaging with the EEL. FIG. 5B depicts a sharpened/tapered drug-delivery feature penetrated through the neointima, IEL, and into the media. FIG. 5C depicts a sharpened/tapered drug-delivery feature penetrated through the neointima, IEL, media, and engaging with the EEL. None of the drug-delivery features described above in Example 1 perforated the vessel.

B. Example 2—Stents Having Square Drug-Delivery Features

In this example, a stent having square or rectilinear drug-delivery features was placed within a blood vessel of a human cadaver. Following placement of the square drug-delivery feature stent, the vessel was removed from the cadaver, embedded in plastic, and sliced into cross-sections of a thickness suitable for histology. The cross-sections were stained using an Elastic Masson Trichrome stain, imaged, and evaluated for the positioning of the square drug-delivery feature stent in the vessel.

Figure 6A:
FIGS. 6A-6O are cross-sectional images of a portion of a blood vessel having a drug-eluting stent with square struts configured in accordance with another embodiment of the present technology expanded therein.
Figure 6B:
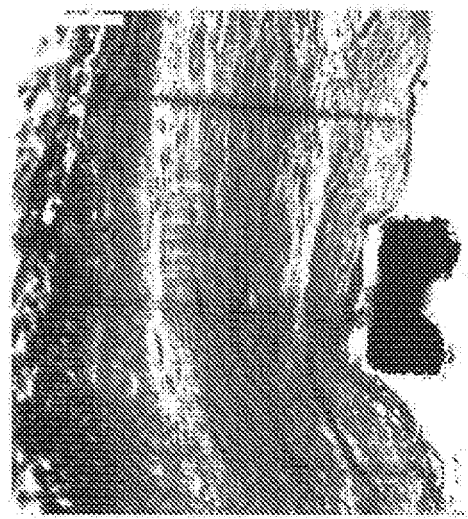
Figure 6C:
Figure 6D:
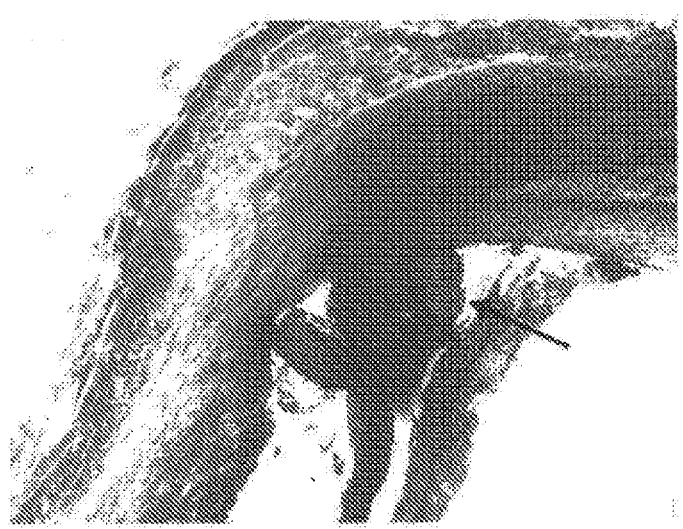
Figure 6E:
Figure 6F:
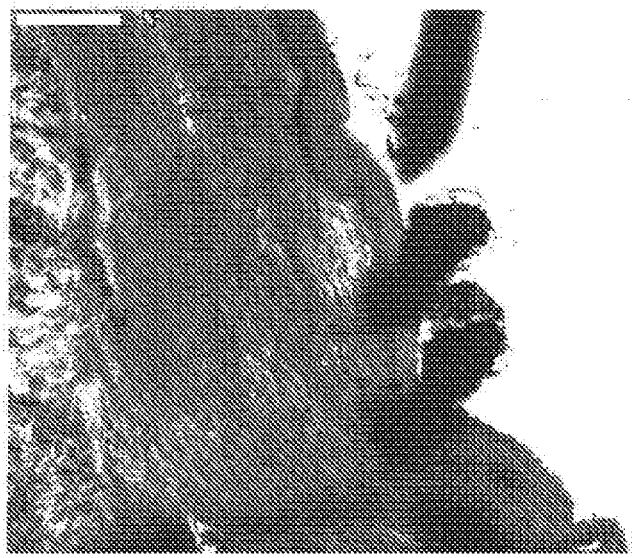
Figure 6G:
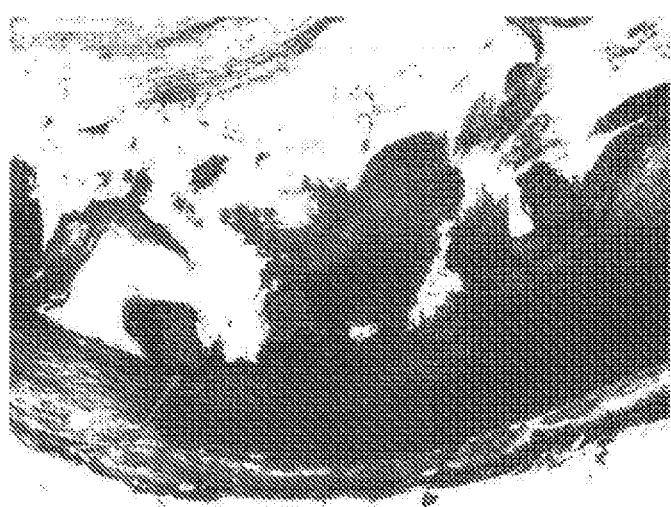
Figure 6H:
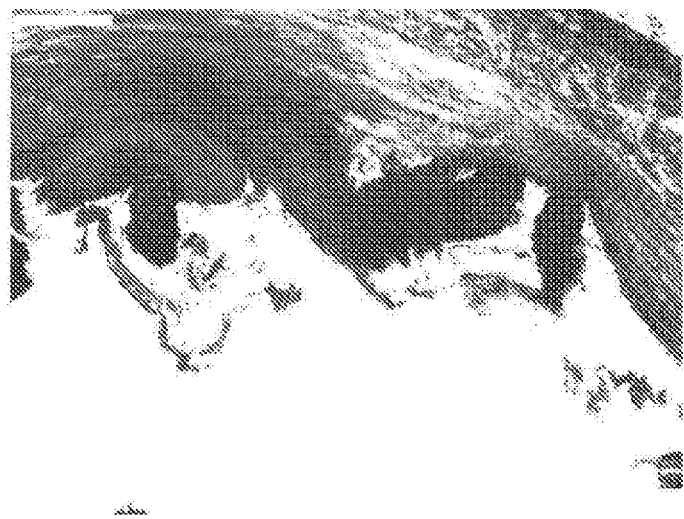
Figure 6I:
Figure 6J:
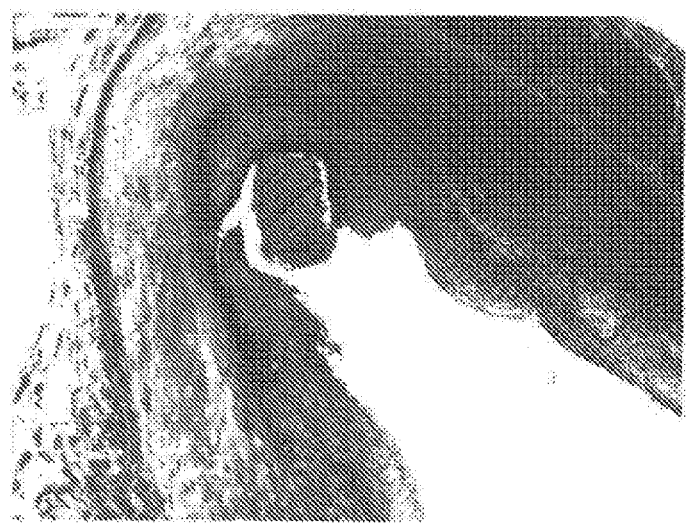
Figure 6K:
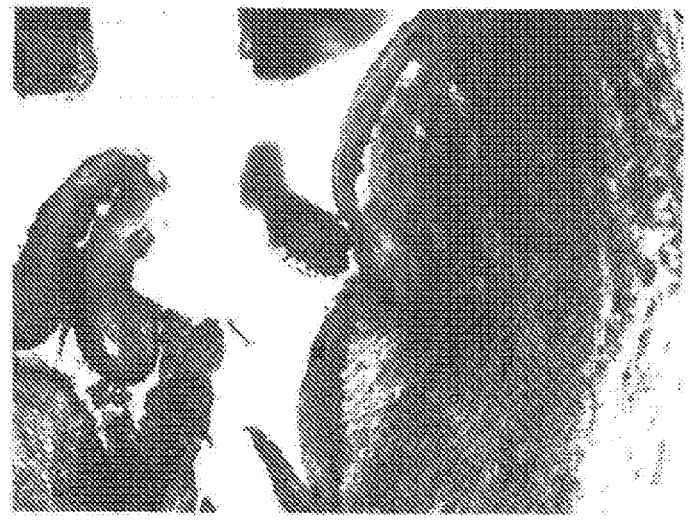
Figure 6L:
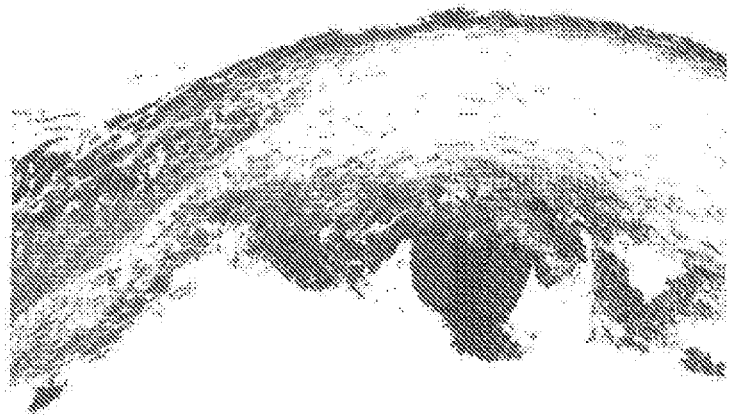
Figure 6M:
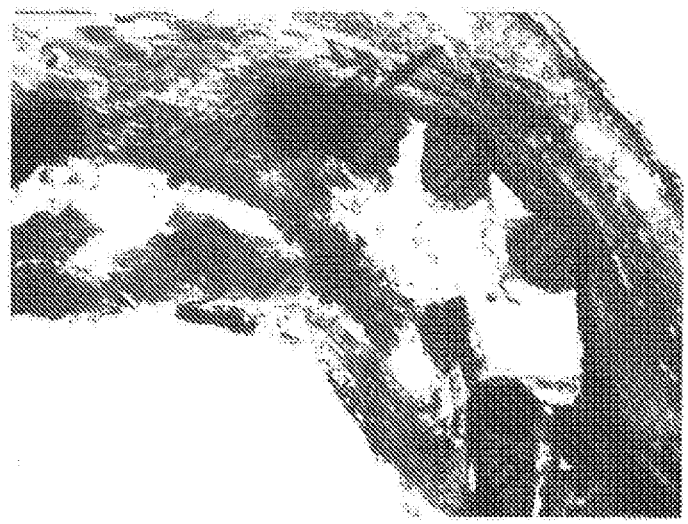
Figure 6N:
Figure 6O:
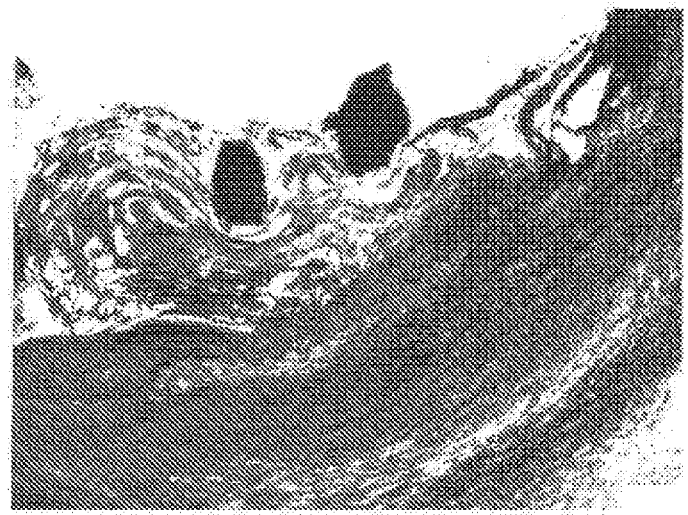

FIGS. 6A-6O include histology images taken after placement of the stent having the square drug-delivery features in a vessel of the cadaver. For example, FIG. 6A depicts a square drug-delivery feature having a width of 96.79 µm and a depth of 115.62 µm. FIGS. 6B and 6C depict two square drug-delivery features with one engaging with the neointima and one pushing the neointima into the IEL. FIG. 6D depicts one square drug-delivery feature with one engaging with the neointima and one engaging with the media. FIG. 6E depicts one square drug-delivery feature with one engaging with the neointima. FIG. 6F depicts three square drug-delivery features with one engaging with the neointima. FIGS. 6G and 6H depict square drug-delivery features pushing the neointima into the IEL FIG. 6I depicts one square drug-delivery feature engaging with the IEL. FIG. 6J depicts square drug-delivery features penetrating the neointima and others pushing the neointima into the IEL. FIG. 6K depicts a square drug-delivery feature engaging with the neointima. FIG. 6L depicts square drug-delivery features penetrating the neointima. FIG. 6M depicts square drug-delivery features engaging the neointima and others penetrating into the intima engaging with the IEL. FIG. 6N depicts square drug-delivery features engaging the neointima. FIG. 6O depicts square drug-delivery features engaging the neointima and others penetrating into the media. None of the drug-delivery features associated with Example 2 perforated the vessel.

C. Example 3—Stents Having Round Drug-Delivery Features

In this example, a stent having round or rounded drug-delivery features was placed within a blood vessel of a human cadaver. Following placement of the round drug-delivery feature stent, the vessel was removed from the cadaver, embedded in plastic, and sliced into cross-sections of a thickness suitable for histology. The cross-sections were stained using an Elastic Masson Trichrome stain, imaged, and evaluated for the positioning of the round drug-delivery feature stent in the vessel.

Figure 7A:
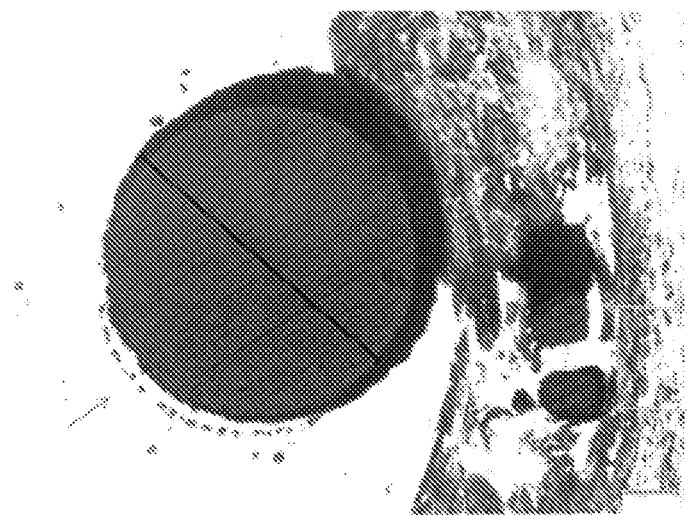
FIGS. 7A-7C are cross-sectional images of a portion of a blood vessel having a drug-eluting stent with round struts configured in accordance with yet another embodiment of the present technology expanded therein.
Figure 7B:
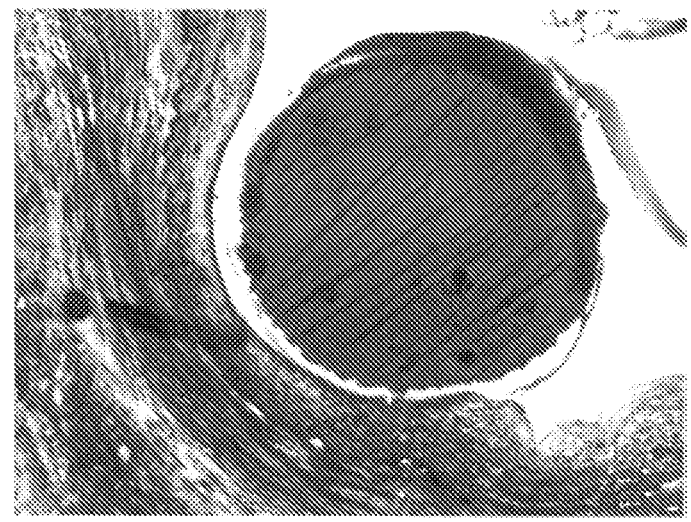
Figure 7C:
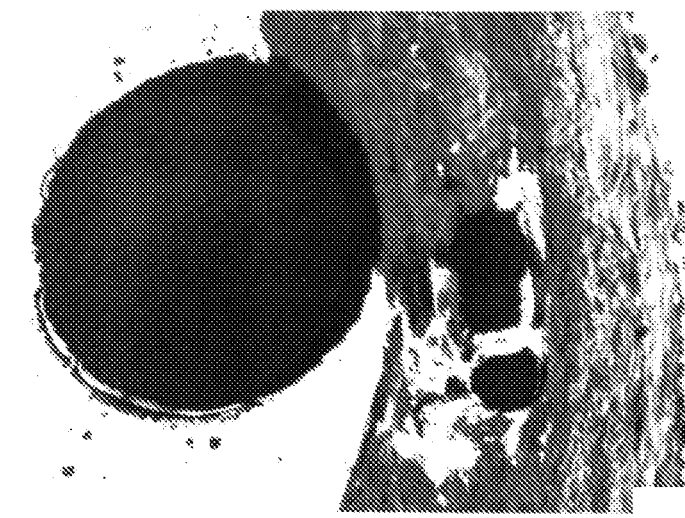

FIGS. 7A-7C include histology images taken after placement of the stent having round drug-delivery features in a vessel of the human patient. FIG. 7A depicts a round drug-delivery feature having a diameter of 651.41 µm. FIG. 7B depicts a round drug-delivery feature engaging with the neointima and pushing the neointima into the IEL FIG. 7C depicts a round drug-delivery feature engaging with the neointima and others penetrating into the media. None of the drug-delivery features associated with Example 3 perforated the vessel.

D. Example 4—Stents Having Sharpened/Tapered Drug-Delivery Features

In this example, a stent having sharpened/tapered drug-delivery features was placed within a blood vessel of a human cadaver. Following placement of the sharpened/tapered drug-delivery feature stent, the vessel was removed from the patient, embedded in plastic, and sliced into cross-sections of a thickness suitable for histology. The cross-sections were stained using an Elastic Masson Trichrome stain, imaged, and evaluated for the positioning of the sharpened/tapered drug-delivery feature stent in the vessel.

Figure 8A:
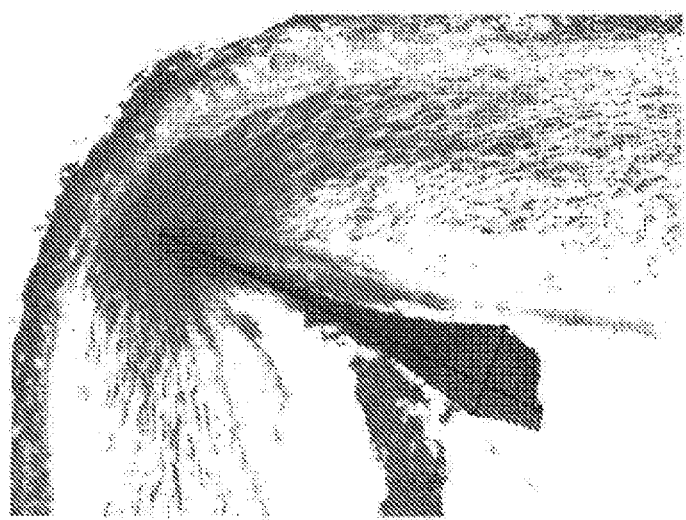
FIGS. 8A-8H are cross-sectional images of a portion of a blood vessel having a drug-eluting stent with pointed struts configured in accordance with still another embodiment of the present technology expanded therein.
Figure 8B:
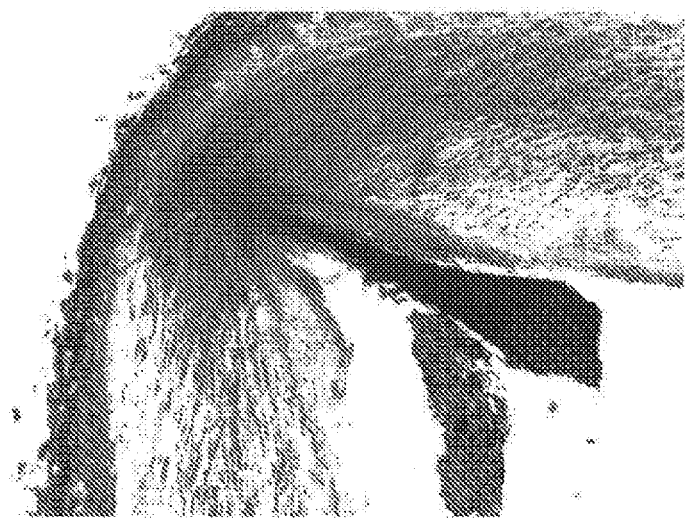
Figure 8C:
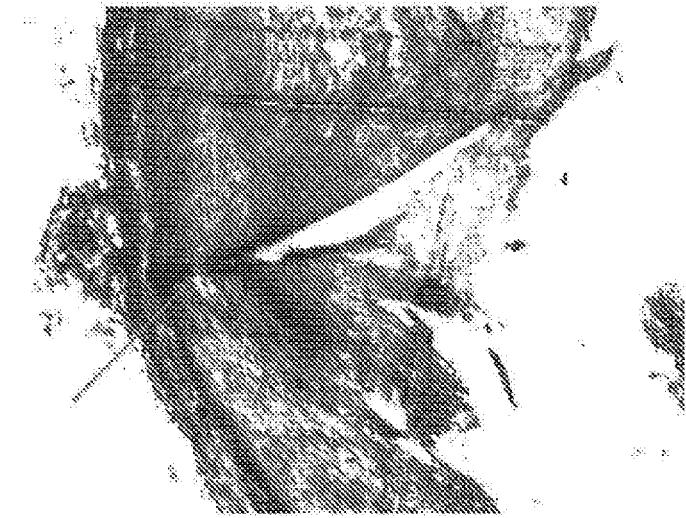
Figure 8D:
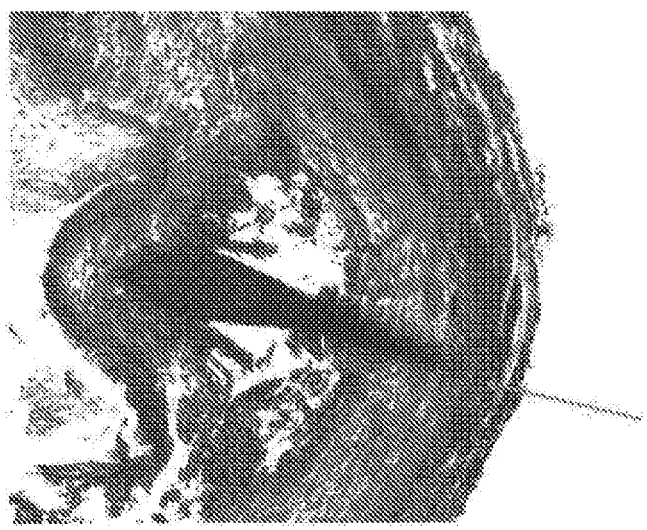
Figure 8E:
Figure 8F:
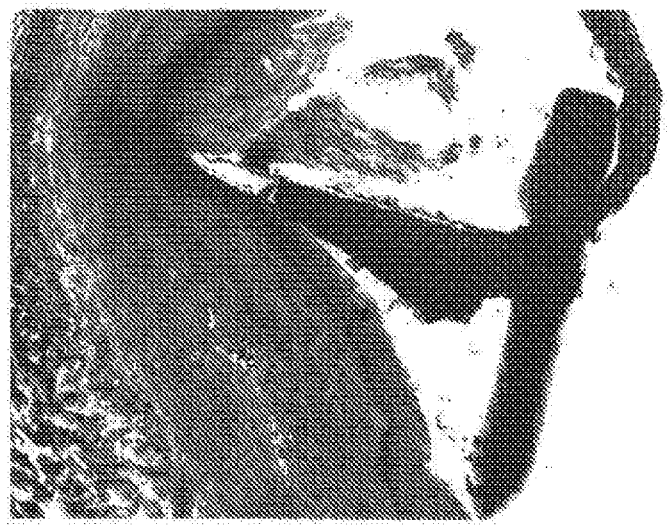
Figure 8G:
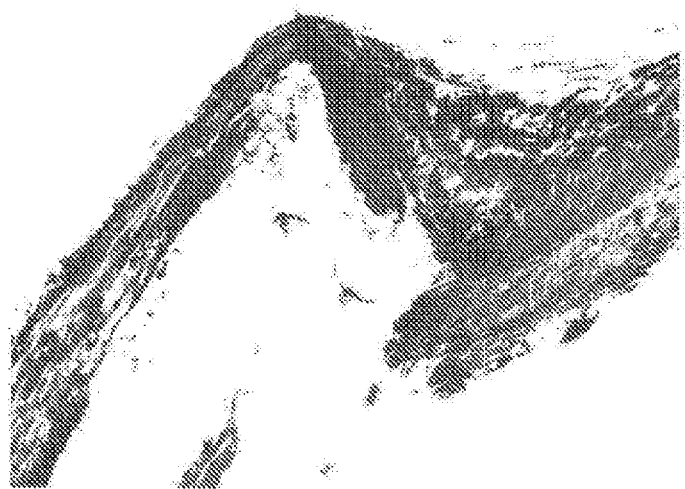
Figure 8H:
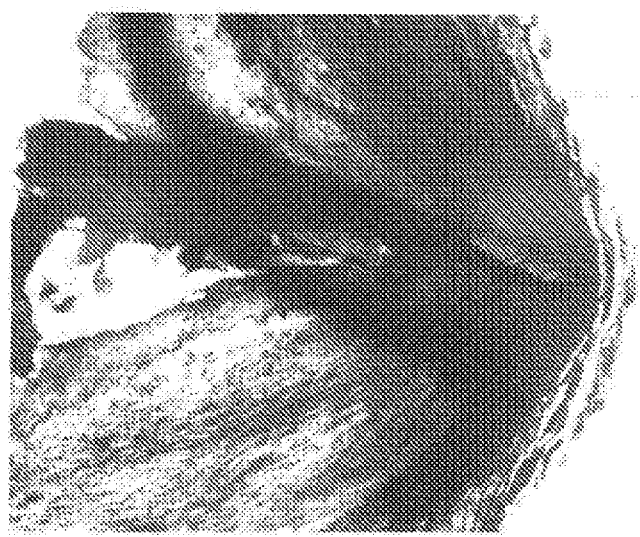

FIGS. 8A-8H include histology images taken after placement of the stent having the sharpened/tapered drug-delivery features in a vessel of the cadaver. FIG. 8A, for example, depicts a sharpened/tapered drug-delivery feature having a maximum width of 193.32 µm and a length of 868.88 µm. FIG. 8B depicts a sharpened/tapered drug-delivery feature penetrating through the neointima, through the IEL, and engaging with the media. FIGS. 8C and 8D depict a sharpened/tapered drug-delivery feature penetrating through the neointima, through the IEL, through the media, and engaging the EEL. FIG. 8E depicts a sharpened/tapered drug-delivery feature penetrating through the neointima, through the IEL, and engaging the media. FIG. 8F depicts a sharpened/tapered drug-delivery feature engaging the neointima. FIG. 8G depicts a sharpened/tapered drug-delivery feature penetrating through the neointima, through the IEL, through the media, and engaging the EEL. FIG. 8H depicts a sharpened/tapered drug-delivery feature penetrating through the neointima, through the IEL, and penetrating the media. None of the sharpened/tapered drug-delivery features described herein with respect to Example 4 perforated the vessel.

E. Example 5—Stents Having Square Drug-Delivery Features Placed Near an Atheroma, Atherosclerotic Lesion, and/or Calcification In this example, a stent having square or rectilinear drug-delivery features was placed within a blood vessel of a human cadaver. Following placement of the square drug-delivery feature stent, the vessel was removed from the patient, embedded in plastic, and sliced into cross-sections of a thickness suitable for histology. The cross-sections were stained using an H&E stain, imaged, and evaluated for the positioning of the square drug-delivery feature stent in the vessel.

Figure 9A:
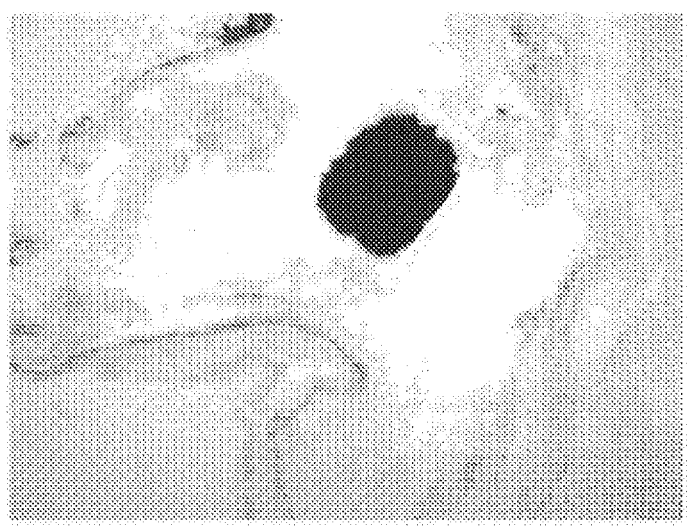
FIGS. 9A-9K are cross-sectional images of a portion of a blood vessel having a drug-eluting stent with square struts configured in accordance with an embodiment of the present technology expanded near an atherosclerotic lesion therein.
Figure 9B:
Figure 9C:
Figure 9D:
Figure 9E:
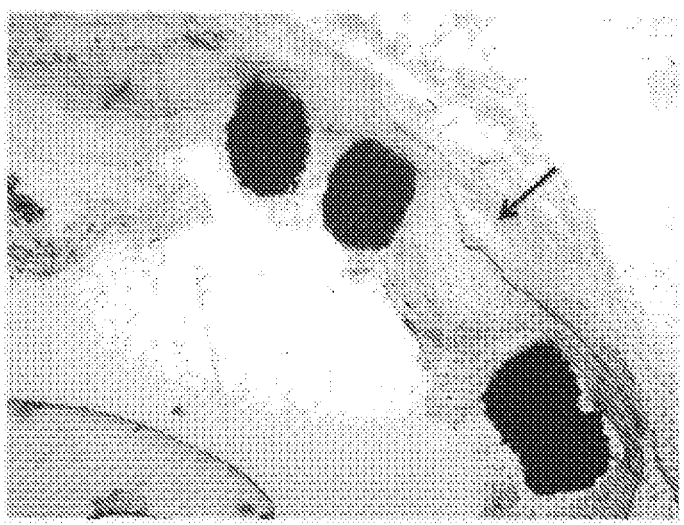
Figure 9F:
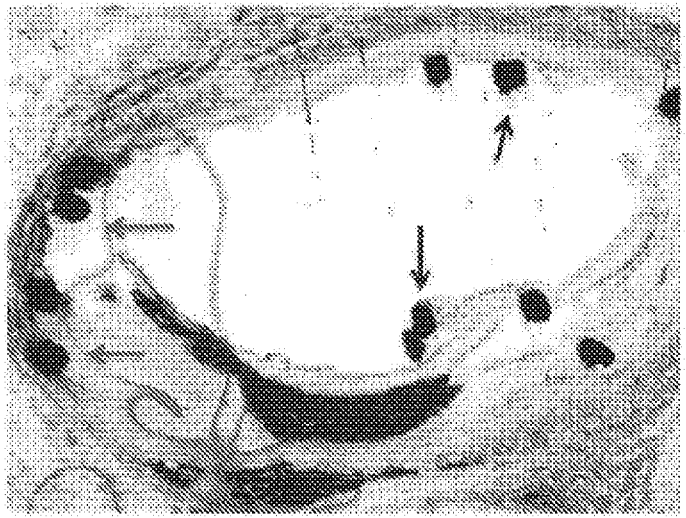
Figure 9G:
Figure 9H:
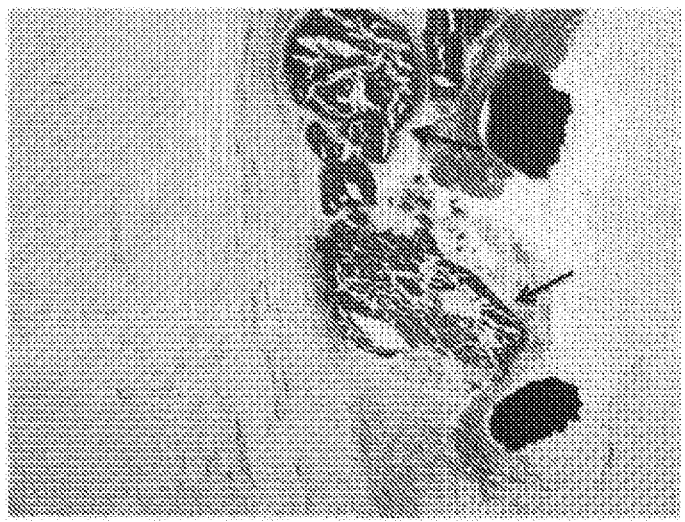
Figure 9I:
Figure 9J:
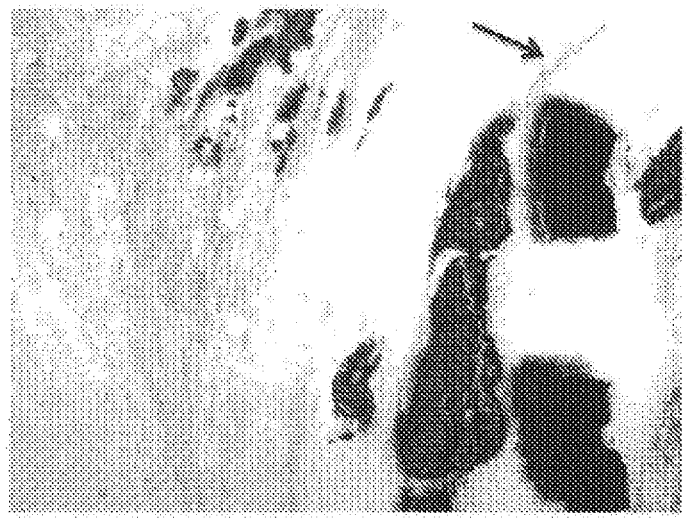
Figure 9K:
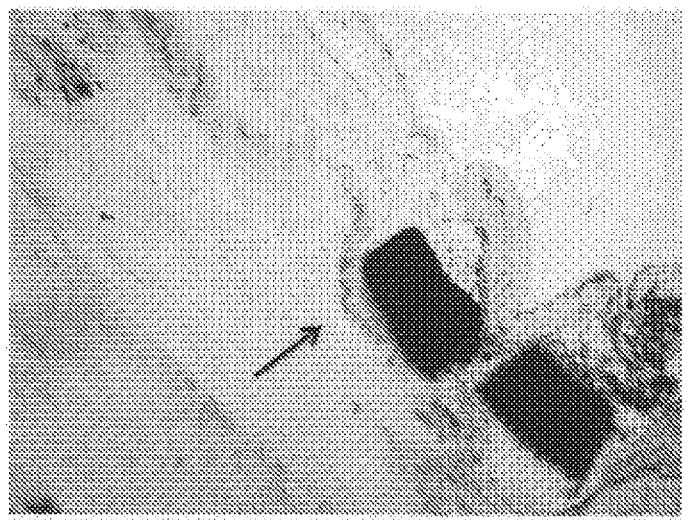

FIGS. 9A-9K include histology images taken after placement of the stent having the square drug-delivery features in a vessel of the cadaver. For example, FIG. 9A depicts a square drug-delivery feature having a width of 248.47 µm and a depth of 292.40 µm. FIG. 9B depicts 22 square drug-delivery features either engaging with the neointima, pushing the neointima into the IEL, or engaging with a plaque having calcifications. FIG. 9C depicts square drug-delivery features engaging with the neointima, engaging with a plaque having calcifications, or engaging with the non-calcified intima. FIG. 9D depicts square drug-delivery features engaging with the IEL and others penetrating the intima and media having calcifications. FIG. 9E depicts square drug-delivery features engaging with the IEL and others pushing the neointima into the IEL. FIG. 9F depicts square drug-delivery features penetrating the neointima and others penetrating the media. FIG. 9G depicts square drug-delivery features engaging with a calcified atheroma, others penetrating the neointima, and another penetrating the media. FIG. 9H is a higher magnification of a portion of the atheroma depicted in FIG. 9G. FIG. 9I depicts square drug-delivery features engaging the neointima and the media of a calcified atherosclerotic plaque. FIG. 9J is a higher magnification of a portion of the atheroma depicted in FIG. 9I. FIG. 9K is a higher magnification of a portion of the atheroma depicted in FIG. 9J. None of the drug-delivery features associated with Example 5 perforated the vessel.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A stent for treating a patient, the stent comprising:
an attachment member;
a frame formed by struts and being radially expandable from a low-profile delivery state to an expanded deployed state at a treatment site within a body lumen of the patient, wherein pairs of the struts are joined together to form intersections, wherein the frame in the expanded deployed state forms an inner lumen extending between a proximal end and a distal end of the frame and providing a fluid pathway along a longitudinal axis of the frame, wherein a diameter of the frame is greater than a diameter of the attachment member and a diameter of the stent decreases along a length thereof such that the frame is collapsible from the deployed state to the delivery state to be retracted within a catheter and withdrawn from the body lumen of the patient; and
multiple protruding features extending from the frame, wherein each of the protruding features includes (a) a proximal portion that extends from a corresponding one of the intersections and in a direction longitudinally away from the attachment member and parallel to the longitudinal axis of the frame and (b) a terminal end portion extending radially away from the frame to engage tissue of the body lumen of the patient while the frame is in the expanded deployed state, the terminal end portion being entirely distal to the proximal portion, each of the protruding features forming a curved shape between the proximal portion and the terminal end portion.

2. The stent of claim 1, wherein, for each of the protruding features, the terminal end portion is positioned entirely distal to the proximal portion.

3. The stent of claim 1, wherein the protruding features carry a drug for delivery to the patient.

4. The stent of claim 1, wherein the protruding features comprise a first set of protruding features configured to deliver a first drug to the patient and a second set of protruding features configured to deliver a second drug to the patient, and wherein the first drug and the second drug are different.

5. The stent of claim 1, wherein the protruding features comprise reservoirs integrally formed therein.

6. The stent of claim 1 wherein the stent is configured to be thermally activated and wherein, when thermally activated, the stent is configured to deliver thermal treatment to the body lumen.

7. The stent of claim 1 wherein the stent is self-expanding.

8. The stent of claim 1 wherein the frame and the protruding features form a single unitary structure.

9. The stent of claim 1 wherein the protruding features are connected to each other only via the frame.

10. The stent of claim 1 wherein the struts are connected to each other to form a circumferential ring that extends continuously about the longitudinal axis.

11. A method for treating a patient, the method comprising:
    delivering a stent within a catheter to a treatment site within a body lumen of the patient, wherein the stent comprises:
        an attachment member;
        a frame formed by struts, wherein pairs of the struts are joined together to form intersections, wherein a diameter of the frame is greater than a diameter of the attachment member and a diameter of the stent decreases along a length thereof; and multiple protruding features extending from the frame;
    advancing the stent out of the catheter;
    expanding the frame from a low-profile delivery state to an expanded deployed state at a treatment site within the body lumen of the patient, the frame forming an inner lumen extending between a proximal end and a distal end of the frame and providing a fluid pathway along a longitudinal axis of the frame, the multiple protruding features extending radially from the frame and engaging tissue of the body lumen of the patient, wherein each of the protruding features includes (a) a proximal portion that extends from a corresponding one of the intersections and in a direction longitudinally away from the attachment member and parallel to the longitudinal axis of the frame and (b) a terminal end portion extending radially away from the frame to engage tissue of the body lumen of the patient while the frame is in the expanded deployed state, the terminal end portion being entirely distal to the proximal portion, each of the protruding features forming a curved shape between the proximal portion and the terminal end portion; and
    retracting the stent from the body lumen of the patient to within the catheter by collapsing the frame from the deployed state to the delivery state.

12. The method of claim 11, wherein expanding the frame comprises expanding the stent with a mechanical actuation mechanism.

13. The method of claim 11, wherein, in the deployed state, the frame comprises an open lattice structure through which a wall of the body lumen is exposed to the inner lumen of the frame.

14. The method of claim 11, the terminal end portion is positioned entirely distal to the proximal portion.

15. The method of claim 11, wherein the protruding features carry a drug for delivery to the patient.

16. The method of claim 11, wherein the expanding comprises piercing a first portion of the body lumen with the protruding features and extending the protruding features into a second portion of the body lumen.

17. The method of claim 16, wherein the first portion of the body lumen is an occlusion, an intima, or a combination thereof.

18. The method of claim 17, wherein the second portion of the body lumen is a media, an adventitia, an internal elastic lamina (IEL), an external elastic lamina (EEL), or a combination thereof.

19. The method of claim 18, wherein the expanding further comprises extending the protruding features into a third portion proximal to the body lumen, the third portion comprising fascia, a different body lumen, or a combination thereof.

20. The method of claim 11, further comprising delivering a drug to the patient from the protruding features.

* * * * *